United States Patent [19]

Leitold et al.

[11] Patent Number: 4,883,796
[45] Date of Patent: Nov. 28, 1989

[54] OXIME ETHERS OF 2,6-DIOXABICYCLO(3.3.0)OCTANONES, AND COMPOSITIONS AND METHODS FOR TREATMENT OF A CARDIAC DISEASE OR CIRCULATORY WITH THEM

[75] Inventors: Matyas Leitold, Biberach; Peter Stoss, Illertissen, both of Fed. Rep. of Germany

[73] Assignee: Heinrich Mack Nachf., Illertissen, Fed. Rep. of Germany

[21] Appl. No.: 151,336

[22] Filed: Feb. 2, 1988

[30] Foreign Application Priority Data

Feb. 13, 1987 [DE] Fed. Rep. of Germany ....... 3704604

[51] Int. Cl.$^4$ .................... A61K 31/34; A61K 31/50; A61K 31/52; C07D 493/04
[52] U.S. Cl. .................... 514/253; 514/265; 514/452; 514/469; 544/268; 544/377; 549/366; 549/464
[58] Field of Search ............... 544/268, 377; 549/366, 549/464; 514/253, 265, 452, 469

[56] References Cited

U.S. PATENT DOCUMENTS

| | | | |
|---|---|---|---|
| 3,584,450 | 11/1982 | Gebert et al. | 514/252 |
| 4,187,313 | 2/1980 | Gschwend et al. | 514/452 |
| 4,235,899 | 11/1980 | Gebert et al. | 514/212 |
| 4,328,227 | 5/1982 | Ulrich et al. | 514/252 |
| 4,469,706 | 9/1984 | Nathanson | 514/657 |
| 4,471,127 | 9/1984 | Huebner et al. | 549/366 |
| 4,542,137 | 9/1985 | Klessing et al. | 514/265 |
| 4,769,379 | 9/1988 | Leitold et al. | 514/290 |

FOREIGN PATENT DOCUMENTS

| | | | |
|---|---|---|---|
| 31266 | 7/1981 | European Pat. Off. | |
| 37777 | 10/1981 | European Pat. Off. | |
| 87378 | 8/1983 | European Pat. Off. | |
| 3602067 | 7/1987 | Fed. Rep. of Germany | 549/464 |

OTHER PUBLICATIONS

Schroeder et al., Pharmazeutische Chemie, pp. 682–691 (1982).
Nicolaus, Symbiotic Approach to Drug Design, Decision Making in Drug Research, 173 (1983).
Leclerc, J. Med. Chem., 23, 620–624 (1980).
Bouzoubaa et al., J. Med. Chem., 27 1291–1294 (1984).
Macchia et al., J. Med. Chem., 28, 153–160 (1985).
Bouzoubaa et al., J. Med. Chem., 28, 896–900 (1985).

*Primary Examiner*—Mukund J. Shah
*Assistant Examiner*—Diana G. Rivers
*Attorney, Agent, or Firm*—Peter C. Richardson; Paul H. Ginsburg; Gezina Holtrust

[57] ABSTRACT

Oxime ethers of 2,6-dioxabicyclo[3.3.0]octanones of the formula I

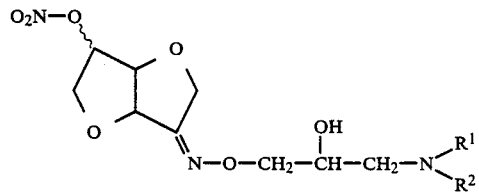

have pharmacological activity and are especially applicable as drugs for the prophylaxis and therapy of cardiac and circulatory diseases.

8 Claims, No Drawings

OXIME ETHERS OF 2,6-DIOXABICYCLO(3.3.0)OCTANONES, AND COMPOSITIONS AND METHODS FOR TREATMENT OF A CARDIAC DISEASE OR CIRCULATORY WITH THEM

BACKGROUND OF THE INVENTION

The majority of the β-receptor blockers therapeutically applied these days are aryloxypropanolamines. Additionally, some are arylethanolamines. Common to both types is an aryl group, i.e. an aromatic system. According to the current opinion of researchers, this aromatic system is a pre-requisite for achieving the desired therapeutic effect (see for example E. Schroder, C. Rufer, R. Schmiechen, Pharmazeutische Chemie, Thieme Verlag 1982, p. 682 ff).

In initial attempts to break through this principle, a possibility was indicated by compounds, in which the aromatic system was "extended outwards" by means of a conjugated double bond. Examples can be found in the following documents: U.S. Pat. No. 4,469,706, DE-OS No. 2 651 084 and EP 31 266.

Subsequently, substances with purely aliphatic basic structures were also manufactured, including substituted oxime ethers, for example J. Med. Chem. 23, 620 (1980); J. Med. Chem. 27, 1291 (1984); J. Med. Chem. 28, 153 (1985); J. Med. Chem. 28, 896 (1985); DE-OS No. 2 658 762; DE-OS No. 2 658 938; EP 37 777; EP 87 378. However, such compounds have had no therapeutic impact so far.

None of the prior art substances have a bicyclic basic structure, let alone one with hetero atoms in the bicyclic ring system. Also, the derivatives known from the literature have no further functional groups in the molecule which could modify or contribute to the overall therapeutic effect. Such added effect was not expected. In the literature, many examples can be found for failed attempts to combine two or more so-called "pharmacophoric groups" in one molecule. In the majority of cases this procedure, occasionally referred to as "chemical hybridisation" or "intramolecular combination", results in the loss of all pharmacological efficacy. The presence of different groups, which are considered pharmacologically active, in one and the same molecule seems to lead mainly to an extinction of activity (see for example B. J. Nicolaus, "Symbiotic Approach to Drug Design", in "Decision Making in Drug Research", Edit. F. Gross, Raven Press, 1983, p. 173 ff.).

It can therefore be regarded as surprising, that this prejudice does not apply to the compounds according to the present invention. These distinguish themselves by a basic structure (2,6-dioxabicyclo-[3.3.0]octanone) hitherto not utilized in this field of indication, and additionally by the presence of both a nitrate ester group and an N-substituted 3-amino-2-hydroxypropyl-oxime ether function. Despite this chemical hybridization, the invention allowes for the creation of pharmaceutically active substances with novel structures, extending the range of application of known compound classes and exploiting new areas of pharmaceutical indication. Completely unexpectedly, the present compounds exhibit a pharmacological efficacy profile that generally can not be matched by other prior art substances.

SUMMARY OF THE INVENTION

The present invention is concerned with new oxime ethers of 2,6-di-oxabicyclo[3.3.0]octanones of the formula I

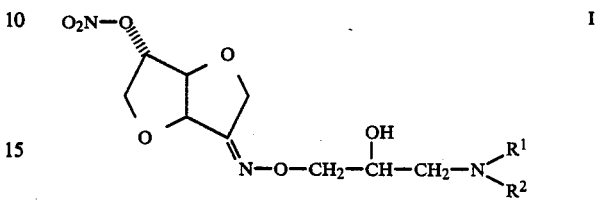

in which $R^1$ and $R^2$ are the same or different and are selected from (a) hydrogen, (b) a straight-chain or branched alkyl group with 1-6 C-atoms, preferably with 3-4 C-atoms, (c) a ω-theophyllin-7-yl-alkyl group, wherein the alkyl group preferably contains 2-3 C-atoms, (d) an unsubstituted or substituted 2,3-dihydrobenzo[1.4]diox-in-2-yl-methyl group, and (e) a benzyl group, or (f) $R^1$ and $R^2$, when taken together with the nitrogen atom to which they are attached, are an unsubstituted or substituted piperazine ring, wherein the substituent may be eihter alkylphenyl or alkoxyphenyl, especially methylphenyl and methoxyphenyl; theophyllin-7-yl or theobromin-1-yl; and salts of inorganic or organic acids, preferably of pharmaceutically acceptable acids.

In formula I, the O—NO$_2$ group can be positioned both endo- and exocyclic to the ring system, as expressed in the formula by means of a corrugated line ( ).

DETAILED DESCRIPTION OF THE INVENTION

The oxime ethers of 2,6-dioxabicyclo[3.3.0]octanones of the formula I of the present invention consist of the endo-isomers of the formula I a

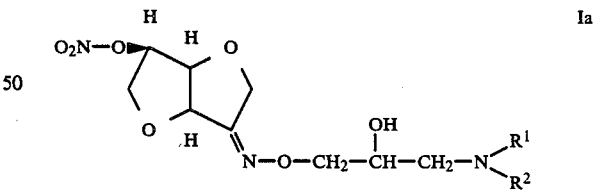

in which $R^1$ and $R^2$ have the meaning indicated above, and the exo-isomers of the formula I b,

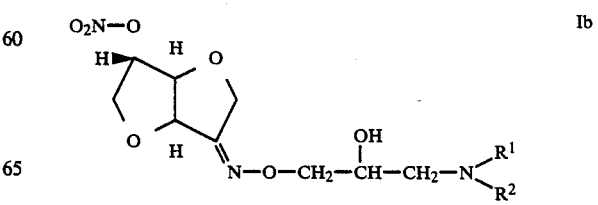

in which $R^1$ and $R^2$ have the meaning indicated above.

Due to the known oxime ether isomerisation, the compounds of formula I according to the present invention can also occur in the stereo-isomeric E- and/or Z-forms.

The N-substituted 3-amino-2-propanol side-chain present in the compounds of general formula I contains a chiral centre. Substances of this type can therefore exist both as racemates and in the form of pure optical antipodes as R- and S-enantiomers. The basic structures of 2,6-dioxabicyclo[3.3.0]octanones are also chiral molecules. For this reason, the compounds of formula I according to the present invention exist as diastereo-isomers.

Both the mixtures of diastereo-isomers and the separated, configuratively uniform components, in the stereo-isomeric E- as well as Z-forms, are the subject of this invention.

2,6-Dioxabicyclo[3.3.0]oxtanones belong to a hitherto rarely investigated class of substances. Ketone derivatives are mentioned only once in the prior art namely in DE-OS No. 3 602 067.

Apart from the bicyclo nomenclature used here, the compounds of the present invention can also be described under the nomenclature for fused ring systems, as hexahydro-furo[3.2-b]furanes.

Among the salts covered by the subject of the invention are those formed with inorganic and organic acids, preferably, however, those formed with pharmaceutically acceptable acids. Examples of these are, hydrochlorides, hydrobromides, nitrates, sulfates, phosphates, acetates, oxalates, maleates, fumarates, tartrates, lactates, maleinates, malonates, citrates, salicylates, methane sulfonates, benzene sulfonates, toluene sulfonates and naphthalene sulfonates.

These or other salts of the present novel compounds, as for example picrates may serve for the purification of the free bases by converting the free base into a salt, isolating the salt, if necessary, recrystallizing or otherwise purifying the salt, and subsequently releasing the base from the salt.

The compounds of the formula I may be prepared by one of the following routes:

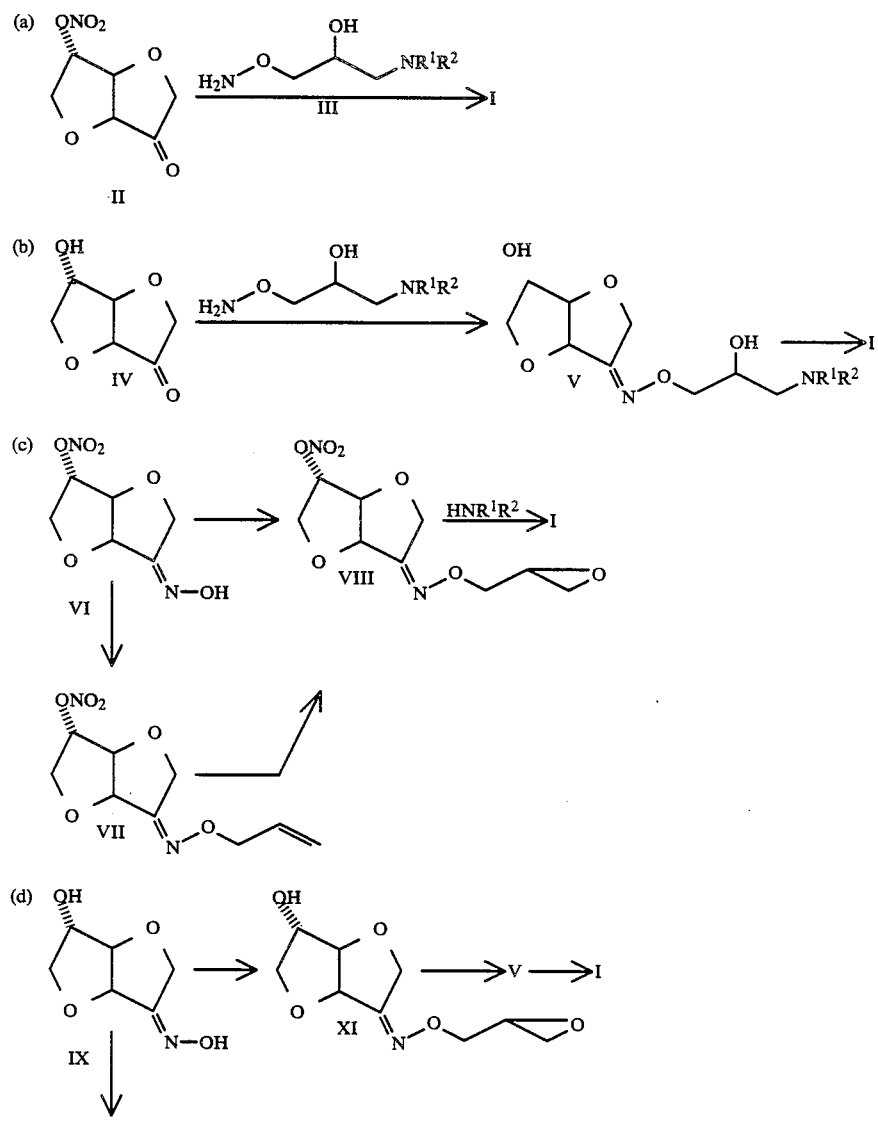

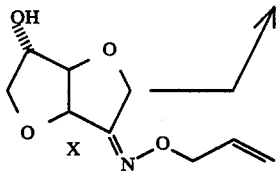

According to route (a) 4-oxo-2,6-dioxabicyclo[3.3.-0]octan-8-endo/exo-ol-nitrate (DE-OS No. 3 602 067) of the formula II is reacted in a well-known manner with an O-substituted hydroxylamine derivative of the formula III, in which $R^1$ and $R^2$ have the meaning indicated above. Such preparative methods are extensively described in the literature and are familiar to persons skilled in the art. Some of the compounds of the general formula III are known (DE-OS No. 2 651 083), others are new intermediates for the synthesis of the compound I of this invention.

In addition, the compound I of this invention can be prepared via route b). This starts by using a corresponding hydroxy-ketone IV (Chem. Ber. 96, 3195 (1963)), which is reacted with the same hydroxylamine derivatives III as in route (a). The reaction products V formed hereby are subsequently converted to the nitrate ester I in the usual way. This synthesis is also based on a method familiar to a skilled person.

A further possibility for the manufacture of the compounds I of the invention is stated in route (c). Here, a 4-hydroximino-2,6-dioxabicyclo[3.3.0]octan-8-endo/exo-ol-nitrate of the formula VI (DE-OS No. 3 602 067) is converted either directly or via the intermediate step of O-allyl-oxime VII into the O-(2,3-epoxypropyl)-oxime VIII and this is subsequently reacted with amines $HNR^1R^2$, in which $R^1$ and $R^2$ have the meaning indicated above. All steps of this synthesis can be carried out using similar methods found in the literature.

Finally, the compounds I of the invention may be obtained via route (d). This is based on hydroxy oximes IX, which are obtainable from the compounds IV in the usual way. The resulting product XI may be prepared either directly or via the intermediate step of O-allyl-oxime X. The synthesis is continued as in route (c), with amines $HNR^1R^2$, thus forming V. This is subsequently converted into the nitrate ester in the usual way. This route also employs well-known reactions and can be readily used by a skilled person without further explanations.

All compounds of the formulae V, VII, VIII, IX, X and XI are not known in the prior art and are therefore novel intermediates for preparation of the compounds I of the invention. The following compounds, for example, may be intermediates:

VII: 4-(O-Allyl-oximino)-2,6-dioxacicyclo[3.3.0]octan-8-endo-ol-nitrate 4-(O-Allyl-oximino)-2,6-dioxabicyclo[3.3.0]octan-8-exo-ol-nitrate VIII: 4-[O-(2,3-Epoxypropyl)-oximino]-2,6-dioxabicyclo[3.3.0]octan-8-endo-ol-nitrate 4-[O-(2,3-Epoxypropyl)-oximino]-2,6-dioxalbicyclo[3.3.0]octan-8-exo-ol-nitrate IX: 4-Hydroximino-2,6-dioxabicyclo[3.3.0]octan-8-endo-ol 4-Hydroximino-2,6-dioxabicyclo[3.3.0]octan-8-exo-ol X: 4-(O-Allyl-oximino)-2,6-dioxabicyclo[3.3.0]octan-8-endo-ol 4-(O-Allyl-oximino)-2,6-dioxabicyclo[3.3.0]octan-8-exo-ol XI: 4-[O-(2,3-Epoxypropyl)-oximino]-2,6-dioxabicyclo[3.3.0]octan-8-endo-ol 4-[O-(2,3-Epoxypropyl)-oximino]-2,6-dioxabicyclo[3.3.0]octan-8-exo-ol The following derivatives of 4-[O-(3-amino-2-hydroxypropyl)-oximino]-2,6-dioxabicyclo[3.3.0]octan-8-endo- and exo-ols serve as examples for the intermediate products V, whereby only the 3-amino substituents are given for each:

3-Isopropylamino
3-tert. Butylamino
3-[4-(2-Methyl-phenyl)-piperazinyl]
3-[4-(2-Methoxy-phenyl)-piperazinyl]
3-(2,3-dihydrobenzo[1.4]dioxin-2-yl-methylamino
3-Theophyllin-7-yl
3-Theobromin-1-yl
3-[2-(7-Theophyllinyl)-ethylamino]
3-[3-(7-Theophyllinyl)-propylamino].

Surprisingly, the compounds according to the present invention distinguish themselves by a wide pharmacological spectrum of activity and can therefore be regarded as valuable medicinal agents. They have cardiac relieving, cardiovascular effects, without inducing a reflectoral increase in the heart rate. They have a hypotensive and spasmolytic effect. In addition, they also have $\beta_1$-receptor blocking properties.

In the following, the many pharmacological effects are illustrated using the compounds of Examples 1 and 3.

In the determination of the orientating toxicity of the compounds of examples 1 and 3, mice withstood 500 mg/kg perorally without exhibiting clinical symptoms and without fatalities.

On isolated aorta strips from rats and rabbits, both substances exhibited dose-dependent inhibition of potassium chloride-induced contractions.

| $ED_{50}$-values (mM/L): | Rat | Rabbit |
|---|---|---|
| Example 1 | 0.024 | 0.0059 |
| Example 2 | 0.472 | 4 |

TABLE 1

Inhibition of Isoprenaline tachycardia in narcotised, despinalised rats after prophylactic, intravenous or intraduodenal application

| Substance | n | Dose mg/kg | $ED_{50}$ mg/kg | 95% Confidence Limits |
|---|---|---|---|---|
| Example 1 i.v. | 9 | 5.0–20.0 | 11.0 | 10.23–16.24 |
| Example 1 i.d. | 9 | 40.0–160.0 | 82.63 | 75.86–98.76 |

TABLE 1-continued

Inhibition of Isoprenaline tachycardia in narcotised, despinalised rats after prophylactic, intravenous or intraduodenal application

| Substance | n | Dose mg/kg | ED$_{50}$ mg/kg | 95% Confidence Limits |
|---|---|---|---|---|
| Example 3 i.v. | 9 | 2.5–10.0 | 4.60 | 3.84–7.48 |
| Example 3 i.d. | 9 | 40.0–160.0 | 74.57 | 66.73–83.33 |

TABLE 2

Influence on the T-wave elevation in the ECG of narcotised rats, which was induced by intravenous bolus injection of Lypressin. The substances were administered perorally 15 minutes and at various times before the Lypressin injection

| Substance | n/Time | Dose mg/kg | ED$_{50}$ mg/kg | 95% Confidence Limits | Length of action at ED$_{50}$-Dose (min.) |
|---|---|---|---|---|---|
| Example 1 | 10 | 20.0–80.0 | 53.76 | 45.56–63.43 | 240 |
| Example 3 | 10 | 20.0–80.0 | 50.82 | 37.62–68.65 | 240 |

TABLE 3

Cardiovascular effects of the compound of example 3 after intravenous administration to narcotised rats (Pentobarbital) with opened thorax and artificial respiration.

| Substance | n | Parameters | Previous Value | Efficacy of the substance | Changes | Maximum efficacy (min) | Length of action (min) |
|---|---|---|---|---|---|---|---|
| Example 3 1.0 mg/kg i.v. | 4 | MAP (mmHg) | 117 ± 5 | 81 ± 5** | −36 ± 20 | 1.2 ± 0.0 | 111 ± 15 |
| | | TPVR (mmHg/ml) | 142 ± 9 | 99 ± 6** | −43 ± 4 | 1.0 ± 1.0 | 13 ± 8 |
| | | BAF (ml/min) | 73 ± 16 | 40 ± 11** | −34 ± 5 | 1.3 ± 0.3 | 109 |
| | | PAP (mmHg) | 22 ± 3 | 17 ± 2 | −5 ± 2 | 3.0 ± 0.1 | 50 ± 18 |
| | | LVP (mmHg) | 130 ± 12 | 92 ± 12** | −38 ± 2 | 1.7 ± 0.4 | 103 ± 28 |
| | | LVEDP (mmHg) | 3.8 ± 1.0 | 3.1 ± 1.0 | 0.7 ± 0.7 | 9.3 ± 8 | 51 ± 28 |
| | | HR (beats/min) | 140 ± 8 | 127 ± 4 | −13 ± 10 | 7 ± 3 | >114 |
| | | CO (l/min) | 0.83 ± 0.04 | 0.74 ± 0.08 | −0.09 ± 0.02 | 5 ± 2 | 113 ± 21 |
| | | SV (ml/min) | 6.0 ± 0.4 | 6.3 ± 0.6 | +0.3 ± 0.5 | 2 ± 1 | 31 ± 24 |
| | | LV dp/dt (mmHg/s) | 2558 ± 141 | 1747 ± 84* | −811 ± 116 | 6.8 ± 5 | 107 ± 12 |

Significant difference compared to the previous value p < 0.05*, p < 0.01**
MAP = mean arterial blood pressure
TPVR = total peripheral vascular resistence
PAP = blood pressure in the A. pulmonalis
LVP = left ventricular blood pressure
CO = cardiac minute volume
SV = cardiac output
BAF = blood flow in the A femoralis
HR = cardiac frequency
LV dp/dt = maximum left ventricular pressure increase rate
LVEDP = left ventricular end diastolic pressure

TABLE 4

Cardiovascular effects of example 3 after i.d. administration to narcotised rats (Pentobarbital) with opened thorax and artificial respiration.

| Substance | n | Parameters | Previous Value | Efficacy of the substance | Changes | Maximum efficacy (min) | Length of action (min) |
|---|---|---|---|---|---|---|---|
| Example 3 30 mg/kg i.d. | 4 | MAP (mmHg) | 116 ± 7 | 91 ± 12** | −25 ± 4 | 58 ± 12 | >167 |
| | | TPVR (mmHg/ml) | 155 ± 8 | 132 ± 10** | −23 ± 3 | 39 ± 5 | >136 |
| | | BAF (ml/min) | 70 ± 4 | 47 ± 23* | −23 ± 5 | 42 ± 8 | >167 |
| | | PAP (mmHg) | 22.8 ± 6 | 18.5 ± 7* | −4.3 ± 5 | 33 ± 11 | 111 ± 16 |
| | | LVP (mmHg) | 133 ± 9 | 95 ± 10** | −38 ± 11 | 65 ± 17 | >153 |
| | | LVEDP (mmHg) | 3.8 ± 1 | 1.5 ± 2* | −2.3 ± 0.9 | 38 ± 27 | 77 ± 8 |
| | | HR (beats/min) | 142 ± 5 | 119 ± 7 | −23 ± 4 | 78 ± 44 | >167 |
| | | CO (l/min) | 0.75 ± 0.03 | 0.66 ± 0.05 | −0.09 ± 0.02 | 62 ± 8 | >167 |
| | | SV (ml/min) | 5.3 ± 0.4 | 5.8 ± 0.3 | +0.5 ± 0.07 | 33 ± 3 | >167 |
| | | LV dp/dt (mmHg/s) | 2345 ± 100 | 1466 ± 189** | −879 ± 90 | 76 ± 10 | >132 |

Significant difference compared to the previous value p < 0.05*, p < 0.01**
MAP = mean arterial blood pressure
TPVR = total peripheral vascular resistence
PAP = blood pressure in the A. pulmonalis
LVP = left ventricular blood pressure
CO = cardiac minute volume
SV = cardiac output
BAF = blood flow in the A femoralis
HR = cardiac frequency
LV dp/dt = maximum left ventricular pressure increase rate
LVEDP = left ventricular end diastolic pressure

TABLE 5

Influence on the systolic arterial pressure (SAP) and the heart rate (HR) of concious normotensive beagle dogs. Substance was administered perorally.

| Substance | n | Dose mg/kg | Measuring Parameters | Influence of the substances on blood pressure and heart rate at different times (h) | | | | | |
|---|---|---|---|---|---|---|---|---|---|
| | | | | 0 | 0.5 | 1 | 2 | 3 | 4 |
| Example 3 | 4 | 5.0 | SAP (mmHg) | 137 ± 7 | 109 ± 4 | 106 ± 2 | 116 ± 5 | 122 ± 4 | 128 ± 7 |
| | | | Changes (mmHg) | | −28 ± 6** | −31 ± 5** | −21 ± 2* | −15 ± 4* | −9 ± 3 |
| | | | HR (Schl/M) | 95 ± 8 | 82 ± 7 | 75 ± 5 | 70 ± 6 | 76 ± 4 | 81 ± 4 |
| | | | Changes (Schl/M) | | −13 ± 2* | −20 ± 5* | −24 ± 6* | −19 ± 5* | −14 ± 4* |
| Example 1 | 4 | 10.0 | SAP (mmHg) | 134 ± 3 | 98 ± 3*** | 102 ± 4**** | 114 ± 3*** | 118 ± 3* | 115 ± 3* |
| | | | Changes (mmHg) | | −36 ± 2 | −32 ± 2 | −20 ± 1 | −16 ± 2 | −19 ± 3 |
| | | | HR (Schl/M) | 88 ± 3 | 73 ± 3 | 72 ± 5 | 74 ± 6 | 78 ± 4 | 79 ± 5 |
| | | | Changes (Schl/M) | | −15 ± 3* | −16 ± 4* | −14 ± 2* | −10 ± 3* | −9 ± 2* |

Significant difference compared to initial value $p < 0.05*$, $p < 0.01$, $p < 0.0001*$

TABLE 6

Reduction of the arterial mean pressure in narcotised rabbits. The substance was administered i.d.

| Substance | n | Dose mg/kg | $ED_{30}$ (mmHg) mg/kg | 95% Confidence Limits |
|---|---|---|---|---|
| Example 1 | 9 | 8.0–32.0 | 24.23 | 14.06–41.76 |
| Example 3 | 9 | 8.0–32.0 | 22.82 | 16.03–32.49 |

The invention is also concerned with the application of compounds of the formula I and their salts as medicinal agents, especially for the treatment and prophylaxis of cardiac and circulatory diseases. The drug formulation contains at least one compound of the formula I, if desired in the form of one of the compound's physiologically tolerable acid addition salts, as active substance and can be administered either alone or mixed with suitable carrier substances. Such drugs could contain the compounds of the invention or the salts thereof in a weight content of 0.1 to 99.9%. The dosage can be chosen as desired and may lie in the range of 1 mg to 500 mg.

All formulations known to those skilled in the art are suitable. Examples of suitable pharmaceutical application forms are suppositories, powders, granulates, tablets, capsules, suspensions, liquids, parenterals and transdermal systems. Solid, semi-solid or liquid carrier materials or dilution media can be used in the manufacture of pharmaceutical dosage forms. Included herein are correcting agents, binding agents, lubricants, emulsifiers etc. Examples of such agents are: starch, such as potato and cereal starches, sugar such as lactose, sucrose, glucose, mannitol, sorbitol, celluloses such as crystalline cellulose, methyl cellulose, calcium carboxymethyl cellulose, sodium carboxymethyl cellulose and hydroxypropyl cellulose, inorganic materials such as potassium phosphate, calcium sulfate, calcium carbonate and talc, gelatin, gum arabic, polyvinyl pyrrolidone, surfactant substances such as fatty acid glycerides, fatty acid-sorbitane esters, fatty acid esters of sucrose polyglycerin and others.

Some examples of drug formulations using the compounds of the invention are listed as follows:

| Tablets: Composition | mg/tablet |
|---|---|
| Compound of the invention | 3 |
| Microcrystalline cellulose | 25 |
| Lactose | 17 |
| Carboxymethyl cellulose calcium | 4.5 |
| Magnesium stearate | 0.5 |

The above listed ingredients are sieved, carefully and sufficiently mixed, and pressed on a suitable tablet press.

| Capsules: Composition | mg/capsule |
|---|---|
| Compound of the invention | 10 |
| Lactose | 40 |
| Microcrystalline cellulose | 30 |
| Talc | 10 |

The above listed ingredients are sieved, carefully and sufficiently mixed and filled into hard gelatin capsules on a suitable capsule filling machine.

The following examples serve to illustrate the invention. Unless otherwise stated, the compounds illustrated in the examples are diastereoisomeric mixtures.

EXAMPLE 1

4-(2-Hydroxy-3-isopropylamino-propyl)-oximino-2,6-dioxabicyclo[3.3.0]octan-8-endo-ol-nitrate (a) O-(2-Hydroxy-3-isopropylamino-propyl)acetohydroximic acid ethyl ester: 15.9 g of O-(2,3-epoxypropyl)-acetohydroximic acid ethyl ester (DE 2 651 085) are heated with 17.7 g of isopropylamine in 100 ml of ethanol for 4 hours under reflux. The solvent and the excess isopropylamine are subsequently removed using a rotary evaporator and the oily residue is distilled under vacuum. Boiling point 71°–73° C./0.2 mm; yield 17.5 g.; $C_{10}H_{22}N_2O_3$ (218.29).

(b) O-(2-Hydroxy-3-isopropylamino-propyl)hydroxylamine-dihydrochloride: 21.2 g of the intermediate product (a) are heated with 150 ml of 2N-HCl for 15 min. under reflux. The solution is evaporated to dryness under reduced pressure and the residue is recrystallized using ethanol. Melting point 166°–167° C.; yield 20.5 g (cf. DE-OS No. 2 651 083); $C_6H_{16}N_2O_2 \cdot 2HCl$ (221.13).

(c) 22.1 g of the compound (b) are added to a solution of 13.8 g of anhydrous potassium carbonate in 1 l of dry methanol and stirred for 5 min at room temperature, in order to release the base. 18.9 g of 4-Oxo-2,6-dioxabicyclo[3.3.0]octan-8-endo-ol-nitrate (DE-OS No. 3 602 067) are added and the mixture is stirred overnight. After filtering off the inorganic salts and removing the solvent the product is recrystallized several times using isopropanol. Yield 21.7 g; melting point 78°–80° C.; $[\alpha]_D^{20} + 172.6$ (c=0.701, acetone); $C_{12}H_{21}N_3O_7$ (319.32).

EXAMPLE 2

4-(2-Hydroxy-3-isopropylamino-propyl)-oximino-2,6-dioxabicyclo[3.3.0]octan-8-exo-ol-nitrate The base is released from 22.1 g of O-(2-hydroxy-3-isopropylamino-propyl)-hydroxylamine dihydrochloride (example 1b), by dissolving in 1 l of methanol, using the stoichiometrical amount of anhydrous potassium carbonate. 18.9 g of 4-Oxo-2,6-dioxabicyclo[3.3.0]octan-8-exo-ol-nitrate (DE-OS No. 3 602 067) are added to this and the whole is stirred overnight at room temperature. After treating in the normal way, the raw base is precipitated as the semioxalate, which is recrystallized using methanol. Yield 26.2 g; melting point 156° C. (decomposition); $[\alpha]_D^{20} + 6.80$ (c=0.741, methanol). $C_{12}H_{21}N_3O_7.0.5C_2H_2O_4$ (364.34).

EXAMPLE 3

4-(3-tert.-Butylamino-2-hydroxy-propyl)-oximino-2,6-dioxabicyclo[3.3.0]octan-8-endo-ol-nitrate (a) O-(3-tert.-Butylamino-2-hydroxy-propyl)acetohydroximic acid ethyl ester: 31.8 g of O-(2,3-epoxypropyl)-acetohydroximic acid ethyl ester are heated with 43.9 g of tert. butylamine in 300 ml of ethanol for 4 hours under reflux. The solvent and the excess tert.-butylamine are subsequently removed on a rotary evaporator and the oily residue is distilled under vacuum. Boiling point 83°–84° C./0.2 mm; yield 40.6 g (cf. DE-OS No. 2 651 083).

(b) O-(3-tert.-butylamino-2-hydroxy-propyl)hydroxylamine-dihydrochloride: 40.6 g of the intermediate product (a) are heated with 150 ml of 2N HCl for 15 min under reflux. The solution is evaporated to dryness under reduced pressure and the residue recrystallized using ethanol. Melting point 194°–195° C.; yield 36.9 g (cf. DE-OS No. 2 651 083): $C_7H_{18}N_2O_2.2HCl$ (235.15).

(c) 16.2 g of the base released from compound (b) are dissolved in 1 l of methanol. After adding 18.9 g of 4-oxo-2,6-dioxabicyclo[3.3.0]octan-8-endo-ol-nitrate, it is stirred overnight at room temperature. Normal treatment and precipitation of the raw base as semioxolate produces colorless crystals, which are recrystallized using isopropanol. Yield 22.0 g; melting point 155°–160° C. (dec.); $[\alpha]_D^{20} + 163.6$ (c=0.583, methanol; $C_{13}H_{23}N_3O_7.0.5C_2H_2O_4$ (378.37).

EXAMPLE 4

4-(3-tert.-Butylamino-2-hydroxy-propyl)-oximino-2,6-dioxabicyclo[3.3.0]octan-8-exo-ol-nitrate 16.2 g of O-(3-tert.butylamino-3-hydroxy-propyl)hydroxyl-amine (example 3b), are dissolved in 1 l of methanol. 18.9 g of 4-Oxo-2,6-dioxabicyclo[3.3.0]octan-8-exo-ol-nitrate are added and the whole is stirred overnight at room temperature. After treating in the normal way, the raw base is precipitated as the semioxalate and this is recrystallized using methanol. Yield 23.3 g; melting point 179° C. (dec.); $[\alpha]_D^{20} + 6.50$ (D=0.655, methanol); $C_{13}H_{23}N_3O_7.0.5C_2H_2O_4$ (378,37).

EXAMPLE 5

4-<3-[4-(2-methoxyphenyl)-1-piperazinyl]-2-hydroxypropyl>-oximino-2,6-dioxabicyclo[3.3.0]octan-8-endo-ol-nitrate (a) O-<3-[4-(2-Methoxyphenyl)-1-piperazinyl]-2-hydroxy-propyl>-acetohydroximic acid ethyl ester: analogous to example 1a) from 15.9 g of O-(2,3-epoxypropyl)-acetohydroximic acid ethyl ester and 19.2 g of 1-(2-methoxyphenyl)piperazine. Melting point 73°–74° C. (using diisopropyl ether); Yield 23.3 g.; $C_{18}H_{29}N_3O_4$ (351.45).

(b) O-<3-[4-(2-Methoxyphenyl)-1-piperazinyl]-2-hydroxy-propyl>-hydroxylamine-trihydrochloride:

from 35.1 g of the aforementioned compound by heating with 2N HCl, analogous to example 1b). Yield 21.9 g; melting point 154°–157° C. (dec.) (cf. DE-OS No. 2 651 083); $C_{14}H_{23}N_3O_3.3HCl.H_2O$ (408.75).

(c) By reacting 28.1 g of base from compound (b) with 18.9 g of 4-oxo-2,6-dioxabicyclo[3.3.0]octan-8-endo-ol-nitrate. Oxalate: yield 31.4 g; melting point 63°–67° C. (using isopropanol); $[\alpha]_D^{20} + 125.5$ (c=1.0, methanol); $C_{20}H_{28}N_4O_8.C_2H_2O_4.0,5H_2O$ (551.51).

EXAMPLE 6

4-<3-[4-(2-Methoxyphenyl)-1-piperazinyl]-2-hydroxypropyl>-oximino-2,6-dioxabicyclo[3.3.0]octan-8-exo-ol-nitrate By reacting 28.1 g of O-3-[4-(2-methoxyphenyl)-1-piperazinyl]-2-hydroxy-propyl-hydroxylamine (base) with 18.9 g of 4-oxo-2,6-dioxabicyclo[3.3.0]octan-8-exo-olnitrate. Oxalate: melting point 90°–93° C. (using ethyl acetate); yield 29.0 g; $[\alpha]_D^{20} + 45.5$ (c=1.0, methanol); $C_{20}H_{28}N_4O_8.C_2H_2O_4$ (542.51).

EXAMPLE 7

4-<3-[4-(2-Methylphenyl)-1-piperazinyl]-2-hydroxypropyl>-oximino-2,6-dioxabicyclo[3.3.0]octan-8-endo-ol-nitrate (a) O-<3-[4-(2-methylphenyl)-1-piperazinyl]-2-hydroxy-propyl>-acetohydroximic acid ethyl ester:

from 15.9 g of O-(2,3-epoxypropyl)acetohydroximic acid ethyl ester and 17.6 g of 1-(2-methylphenyl)-piperazine. The oily product is purified by means of column chromatography on silica gel (mobile phase petroleum ether 50°–70° C./tetrahydrofuran (THF)/methanol, 80/20/2). Yield 30 g.; $C_{18}H_{29}N_3O_3$ (335.45).

(b) O-<3-[4-(2-Methylphenyl)-1-piperazinyl]-2-hydroxy-propyl>-hydroxylamine-trihydrochloride:

from the aforementioned compound by means of hydrolysis with 2N-HCl. Melting point 159°–161° C. (dec.) (using methanol); $C_{14}OH_{23}N_3O_2.3Hcl.3H_2O$ (428.79).

(c) By usual reaction of the base from the aforementioned compound with 4-oxo-2,6-dioxabicyclo[3.3.0]octan-8-endo-ol-nitrate. Oxalate: melting point 58°–62° C.

(using isopropanol); $[\alpha]_D^{20}+116.50$ (c=1.0, methanol); $C_{20}H_{28}N_4O_7 \cdot C_2H_2O_4$ (526.51).

EXAMPLE 8

4-<3-[4-(2-methylphenyl)-1-piperazinyl]-2-hydroxypropyl>-oximino-2.6-dioxabicyclo[3.3.0]octan-8-exo-ol-nitrate Preparation as in the previous examples, from O-<3-[4-(2-methylphenyl)-1-piperazinyl]-2-hyroxy-propyl>-hydroxyl-amine and 4-oxo-2,6-dioxabicyclo[3.3.0]octan-8-exo-ol-nitrate. Oxalate: melting point 85°–88° C. (using isopropanol/ethanol 2:1); $[\alpha]_D^{20}+49.0$ (c=1.0, methanol); $C_{20}H_{28}N_4O_7 \cdot C_2H_2O_4$ (526.51).

EXAMPLE 9

4-[3-(2,3-dihydrobenzo[1.4]-dioxin-2-yl-methylamino)-2-hydroxy-propyl]-oximino-2,6-dioxabicyclo[3.3.0]octan-8-endo-ol-nitrate (a) O-[3-(2,3-dihydrobenzo[1.4]-dioxin-2-yl-methylamino)-hydroxy-propyl]-acetohydroximic acid ethyl ester: from 15.9 g of O-(2,3-epoxy-propyl)-acetohydroximic acid 2-(aminomethyl)-2,3-dihydrobenzo[1.4]dioxin. The oily product was purified by means of column chromatography on silica gel (mobile phase petroleum ether 50°–70° C./THF, 1:1). Yield 15.2 g. $C_{16}H_{24}N_2O_5$ (324,38).

(b) O-[3-(2,3-Dihydrobenzo[1.4]dioxin-2-yl-methylamino)-2-hydroxy-propyl]-hydroxylamine-dihydrochloride: by hydrolysis of (a) with 2NHCl. The substance is extremely hygroscopic; $C_{12}H_{18}N_2O_4 \cdot 2HCl$ (327.22).

(c) By reaction of the base from the aforementioned compound with 4-oxo-2,6-dioxabicyclo[3.3.0]-octan-8-endo-ol-nitrate. Oxalate: melting point 72° C. (using ethanol/methanol 4:1); $[\alpha]_D^{20}+130.0$ (c=1.0, methanol); $C_{18}H_{23}N_3O_9 \cdot C_2H_2O_4$ (515.44).

EXAMPLE 10

4-[3-(2,3-Dihydrobenzo[1.4]-dioxin-2-yl-metylamino)-2-hydroxy-propyl]-oximino-2,6-dioxabicyclo[3.3.0]octan-8-exo-ol-nitrate Manufactured in the usual way from O-[3-(2,3-dihydrobenzo[1.4]dioxin-2-yl-methylamino)-2-hydroxypropyl]-hydroxyylamine and 4-oxo-2,6-dioxabicyclo[3.3.0]octan-8-exo-ol-nitrate. Oxalate: melting point 176°–177° C. (using ethanol): $[\alpha]_D^{20}+50.5$ (c=1.0, methanol); $C_{18}H_{23}N_3O_9 \cdot C_2H_2O_4$ (515.44).

EXAMPLE 11

4-[2-Hydroxy-3-(7-theophyllinyl)-propyl]-oximino-2,6-dioxabicyclo[3.3.0]octan-8-exo-ol-nitrate (a) O-[2-Hydroxy-3-(7-theophyllinyl)-propyl]acetohydroximic acid ethyl ester: from 15.9 g O-(2.3-epoxypropyl)-aceto-hydroximic acid ethyl ester and 18.0 g theophylline in ethanol. The colorless crystalline raw product was used directly in the next step; $C_{14}H_{21}N_5O_5$ (339.35).

(b) O-[2-hydroxy-3-(7-theophyllinyl)-propyl]hydroxylamine-hydrochloride: from the aforementioned compound by means of hydrolysis with 2N HCl. Recrystallization during isopropanol produced hygroscopic crystals which were immediately processed further; $C_{10}H_{15}N_5O_4 \cdot HCl$ (305.72).

(c) By reaction of the free base from (b) with 4-oxo-2,6-dioxabicyclo[3.3.0]octan-8-exo-ol-nitrate. Hydrochloride: melting point: 140°–143° C. (dec.) (using chloroform); $[\alpha]_D^{20}+60.0$ (c=1.0, methanol); $C_{16}H_{20}N_6O_9 \cdot HCl$ (476.83).

EXAMPLE 12

4-[2-hydroxy-3-(1-theobrominyl)-propyl]-oximino-2,6-dioxabicyclo[3.3.0]octan-8-exo-ol-nitrate (a) O-[2-Hydroxy-3-(1-theobrominyl)-propyl]acetohydroximic acid ethyl ester: from 15.9 g of O-(2,3-epoxypropyl)-acetohydroximic acid ethyl ester and 18.0 g of theobromine, a crystalline product is obtained which was processed further without purification; $C_{14}H_{21}N_5O_5$ (339.35).

(b) O-[2-Hydroxy-3(1-theobrominyl)-propyl]hydroxylamine-hydrochloride: from the aforementioned compound by means of hydrolysis with 2N-HCl. Using ethanol, a crystalline, hygroscopic substance was obtained which is incorporated into the next step in this form; $C_{10}H_{15}N_5O_4 \cdot HCl$ (305.72)

(c) By reaction of the base from (b) with 4-oxo-2,6-dioxabicyclo[3.3.0]octan-8-exo-ol-nitrate. The substance crystallized with 0.25 mol 2-propanol. Melting point 99°–100° C. (using 2-propanol); $[\alpha]_D^{20}+57.5$ (c=1.0, methanol); $C_{16}H_{20}N_6O_9$ (440.38).

EXAMPLE 13

4-3-[N-Benzyl-N-(3-<7-theophyllinyl>-propyl)]-amino-2-hydroxy-propyl-oximino-2,6-dioxabicyclo[3.3.0]octan-8-exo-ol-nitrate (a) O-3-[N-Benzyl-N-<3-(7-theophyllinyl)-propylamino>-2-hydroxy-propyl]-acetohydroximic acid ethyl ester: from 15.9 g of O-(2,3-epoxypropyl)-acetohydroximic acid ethyl ester and 32.7 g of 7-(3-benzylamino-propyl)-theophylline. The oily raw product was reacted further without purification; $C_{24}H_{35}N_6O_5$ (487.58).

(b) O-2-Hydroxy-3-[N-Benzyl-N-<3-(7-theophyllinyl)-propyl>]-amino-propyl-hydroxylaminedihydrochloride: by hydrolysis of the aforementioned compound with 2N-HCl. The crystalline raw product was directly reacted further; $C_{20}H_{28}N_6O_4 \cdot 2HCl$ (489.40).

(c) By reaction of the free base from (b) with 4-oxo-2,6-dioxabicyclo[3.3.0]octan-8-exo-ol-nitrate. 1,5hydrochloride.0,5H$_2$O: melting point 89° C. (dec.) (using isopropanol); $[\alpha]_D^{20}+45.0$ (c=1.0, methanol); $C_{26}H_{33}N_7O_9 \cdot 1.5HCl \cdot 0.5H_2O$ (651.29).

EXAMPLE 14

4-2-Hydroxy-3-[3-(7-theophyllinyl)-propyl]-aminopropyl-oximino-2,6-dioxabicyclo[3.3.0]octan-8-exo-ol-nitrate (a) O-3-[N-<3-(7-theophyllinyl)-propyl>-amino]-2-hydroxy-propyl-acetohydroximic acid ethyl ester: from 15.9 g of O-(2,3-epoxypropyl)-acetohydroximic acid ethyl ester and 23.7 g of 7-(3-aminopropyl)theophylline. The oily raw product was reacted further without further purification; $C_{17}H_{28}N_6O_5$ (396.45).

(b) O-[2-Hydroxy-3-<-3-(7-theophyllinyl)-propylamino>-propyl]-hydroxylamine-dihydrochloride: by hydrolysis of (a) wit 2N-HCl. The crystalline product obtained using ethanol was immediately processed further; $C_{13}H_{22}N_6O_4 \cdot 2HCl$ (399.28).

(c) By reaction the free base from (b) with 4-oxo-2,6-dioxobicyclo[3.3.0]octan-8-exo-ol-nitrate. Hydrochloride.0.5H$_2$O: melting point 89°–92° C. (dissolved in chloroform, precipitated with ether); $[\alpha]_D^{20} + 49.0$ (c=1.0, methanol); $C_{19}H_{27}N_7O_9 \cdot HCl \cdot 0.5H_2O$ (542.94).

EXAMPLE 15

4-{2-Hydroxy-3-[2-(7-theophyllinyl)-ethyl]-aminopropyl}-oximino-2,6-dioxabicyclo[3.3.0]-octan-8-exo-ol-nitrate (a) O-{3-[N-2-(7-theophyllinyl)-ethyl-amino-2-hydroxy-propyl}-acetohydroximic acid ethyl ester: from 15.9 g of O-(2,3-epoxypropyl)-acetohydroximic acid ethyl ester and 22.3 g of 7-(2-aminoethyl)-theophylline. The oily raw product was processed further without purification; $C_{16}H_{26}N_6O_5$ (382.42).

(b) O-[2-Hydroxy-3-<2-(7-theophyllinyl)-ethylamino>-propyl]-hydroxylaminee-dihydrochloride. By hydrolysis of (a) with 2N HCl. Using ethanol, a crystalline product was obtained which was processed further in this form; $C_{12}H_{20}N_6O_4 \cdot 2HCl$ (385.25).

(c) By reaction of the free base from (b) with 4-oxo-2,6-dioxabicyclo[3.3.0]octan-8-exo-ol-nitrate. Semioxalate: melting point 174° C. (using methanol) $[\alpha]_D^{20} + 52.5$ (c=1.0, water); $C_{18}H_{25}N_7O_9 \cdot 0.5C_2H_2O_4$ (528.46).

We claim:

1. Oxime ethers of 2,6-dioxabicyclo[3.3.0]octanones of the formula I,

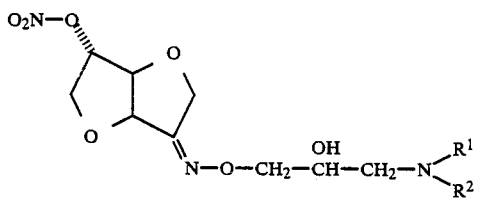

in which
R$^1$ and R$^2$ are the same or different and are selected from
(a) hydrogen,
(b) a straight-chain or branched alkyl group with 1-6 C-atoms,
(c) an ω-theophyllin-7-yl-C$_2$-C$_3$-alkyl agroup,
(d) an unsubstituted or substituted 2,3-dihydrobenzo[1,4]dioxin-2-yl methyl group,
(e) a benzyl group, or
2 (f) R$^1$ and R$^2$, when taken together with the nitrogen atom to which they are attached, are piperazine, optionally substituted by alkyl, phenyl or methoxyphenyl; theophyllin-7-yl; or theobromin-1-yl; and the salts of inorganic or organic acids.

2. A compound according to claim 1 wherein said compound is in the endo-form of the formula Ia,

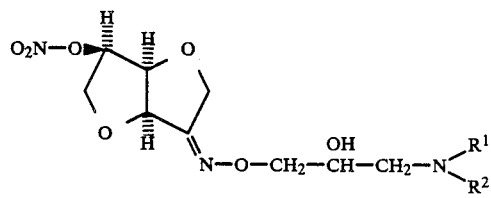

in which R$^1$ and R$^2$ are as defined in claim 1, and the salts thereof.

3. A compound according to claim 1 wherein said compound is in the exo-form of the formula Ib,

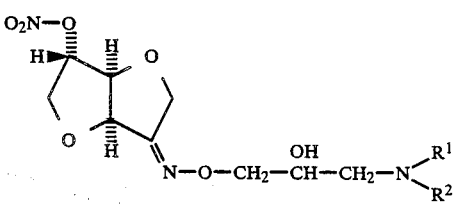

in which R$^1$ and R$^2$ are as defined in claim 1, and the salts thereof.

4. A compound according to claim 1, in all possible position isomeric and stereo isomeric forms, as E- and-/or Z-isomers, as diastereo isomers, and as mixtures thereof, including their salts.

5. A compound according to claim 1 wherein at least one of R$^1$ and R$^2$ is a straight-chain or branched alkyl group of three or four carbon atoms.

6. A compound according to claim 1 wherein said inorganic or organic acid is pharmaceutically acceptable.

7. A pharmaceutical composition for the treatment of a cardiac or a circulatory blood disease which comprises a compound according to claim 1 in an amount effective for the treatment of said disease, and a pharmaceutically acceptable carrier.

8. A process for the treatment of a cardiac disease or a circulatory disease which comprises administering to a patient in need of such treatment a compound according to claim 1 in an amount effective for such treatment.

* * * * *